United States Patent [19]

Finger

[11] Patent Number: Plant 6,878

[45] Date of Patent: Jun. 27, 1989

[54] KALANCHOE PLANT NAMED FANTASY

[75] Inventor: Hermann Finger, Wiesmoor, Fed. Rep. of Germany

[73] Assignee: Wiesmoor-Gartnerie und Baumschule GmbH, Wiesmoor, Fed. Rep. of Germany

[21] Appl. No.: 162,610

[22] Filed: Mar. 1, 1988

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A Kalanchoe plant named Fantasy, having abundant large carmine purple flowers, ideal growth rate, leaf size and self branching for 10 cm pot production, a compact upright growth and resistance to mildew.

1 Drawing Sheet

The present invention relates to a new and distinctive cultivar of Kalanchoe plant, botanically known as *Kalanchoe blossfeldiana,* and known by the cultivar name Fantasy. Fantasy was discovered by me as a mutation of Fascination (U.S. Plant Pat. No. 5,889) in Wiesmoor, Federal Republic of Germany.

Asexual reproduction of stem cuttings of Fantasy by me in Wiesmoor, Federal Republic of Germany has shown that the unique features of this new Kalanchoe are stabilized and are reproduced true to type in successive propagations.

The following characteristics distinguish the new Kalanchoe from other cultivated Kalanchoes of this type known and used in the floriculture industry:

1. Fantasy is characterized by its carmine purple flowers compared to the bright pink flowers of Charme (disclosed in a pending application), the lavender purple (lilac) flowers of Fascination, the rose pink flowers of Satisfaction (U.S. Plant Pat. No. 5,894), and the rose-red flowers of Cherry Jubilee (U.S. Plant Pat. No. 5,877).

2. Fantasy is not as self-branching as Charme and Satisfaction, especially from the basal area, but is similar in branching habit to Fascination and Cherry Jubilee.

3. Leaf size of Fantasy is similar to Fascination and Charme, with Cherry Jubilee and Satisfaction having slightly larger leaves.

4. Leaf color and margins are similar for Fantasy, Charme, Fascination, and Satisfaction, with Cherry Jubilee having somewhat lighter green leaves and a more pronounced crenation of the leaf margin.

5. Fantasy is slightly taller than Charme; is similar in height to Fascination; and is shorter than Satisfaction and Cherry Jubilee.

6. Fantasy has larger, more rounded flowers than Charme, with Fascination and Cherry Jubilee having similar size and shape of flowers. Satisfaction has the same size flower but is more cuspidate at the tip.

7. Flowering time is 10 weeks in summer and 11 weeks in winter, which is similar to Fascination, with Cherry Jubilee and Satisfaction being one week earlier.

8. Growth rate, leaf size and self-branching make this cultivar ideal for 10 cm pot production.

9. Fantasy has similar length of pedicels to Charme, Cherry Jubilee, and Fascination, resulting in a light flower head on the plant with Satisfaction having longer pedicels, resulting in a more open flower head.

The accompanying colored photograph illustrates the overall appearance of Fantasy, with colors being as true as it is reasonably possible to obtain in a colored reproduction of this type.

The following is a detailed description of my new Kalanchoe variety based on plants produced under commercial practices in Wiesmoor, Federal Republic of Germany and Ashtabula, Ohio under greenhouse conditions. Color references are made to The Royal Horticultural Society Colour Chart, except where general colors of ordinary dictionary significance are used.

Parentage: Mutation of Fascination.

Propagation:

(A) *Type cutting.*—Stem tip cuttings up to 2 cm long.

(B) *Time to root.*—10 days at 21° C. summer. 14 days at 21° C. winter.

(C) *Rooting habit.*—Abundant; fine, fibrous roots.

Plant description:

(A) *Form.*—Short, compact, upright growth. Scheduling practices can produce a small plant in a 10 cm pot or a larger plant in a 12 cm pot.

(B) *Habit of growth.*—Excellent basal branching from every node, thus giving a full appearance in the pot with no open space at the bottom. Vigorous growing plant.

(C) *Foliage.*—Leaves simple, opposite (1) Size: Mature leaf 110 mm long and 70 mm wide. However, environment can affect the size of the leaf. (2) Shape: Oblong to ovate, apex obtuse, base acute. (3) Texture: Glabrous, succulent, coriaceous. (4) Margin: Slightly crenate, with some leaves almost undulate. (5) Color: Young foliage, top side 146A, under side 146B. Mature foliage, top side 147A, under side between 147A and B.

Flowering description:

(A) *Flowering habits.*—Inflorescence in a cyme. Flowers start opening with the terminal flower of the main axis first, followed by terminal flowers of the side branches and continuing with subsequent development of branches in the inflorescence.

(B) *Natural flowering season.*—Early January. Flowering time under controlled daylength at 20° C. in summer is 10 weeks; in winter 11 weeks.

(C) *Flower buds.*—Elliptical to oblong, up to 8 mm long, developing to tubular as flower petals mature, sheathed with four green sepals; corolla at maturity is 8 mm long.

(D) *Flowers borne.*—On compound dichasial cymes, primary peduncles 5 mm in diameter, but varying in length depending on growing conditions and B-9 application. Pedicles are up to 6 mm long.

(E) *Quantity of flowers.*—Highly floriferous; main axis contains over 150 flowers with side branches adding up to 50 flowers each.

(F) *Petals.*—(1) Shape: Nearly rounded, top mucronate. (2) Color: Top side, when opening, slightly darker than 57B, fading to 57C and; under side 55A. (3) Number of petals: 4.

(G) *Reproductive organs.*—(1) Stamens: Eight (8) in number. (a) Anther shape: Flat, elliptical, color yellow. (b) Filament color: Whitish green. (c) Pollen color: Yellow. (2) Pistels: (a) Stigma shape: Flat, color greenish white. (b) Style color: Light green. (c) Ovaries: 4 in number, size 5 mm, color medium green.

Disease resistance: No diseases or physiological problems observed to date. Is resistant to mildew.

Other important characteristics: Fantasy has very good keeping qualities, is highly floriferous, does not heat delay under high temperatures during black shade treatment for flowering; flowers fade to a pleasant color.

I claim:

1. The new and distinct cultivar of Kalanchoe plant named Fantasy, as illustrated and described, and parts thereof.

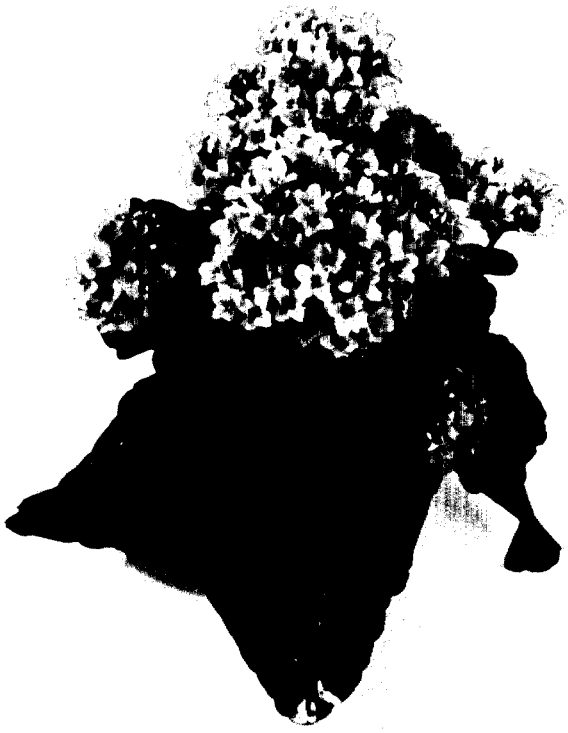

* * * * *